US007618426B2

(12) United States Patent
Ewers et al.

(10) Patent No.: US 7,618,426 B2
(45) Date of Patent: Nov. 17, 2009

(54) APPARATUS AND METHODS FOR FORMING GASTROINTESTINAL TISSUE APPROXIMATIONS

(75) Inventors: Richard C. Ewers, Fullerton, CA (US); Boris Reydel, West Caldwell, NJ (US); Cang Lam, Irvine, CA (US); Eugene Chen, Carlsbad, CA (US); Brent D. Seybold, Santa Clara, CA (US); Rodney Brenneman, San Juan Capistrano, CA (US); Vahid C. Saadat, Saratoga, CA (US)

(73) Assignee: USGI Medical, Inc., San Clemente, CA (US)

( * ) Notice: Subject to any disclaimer, the term of this patent is extended or adjusted under 35 U.S.C. 154(b) by 463 days.

(21) Appl. No.: 10/639,162

(22) Filed: Aug. 11, 2003

(65) Prior Publication Data

US 2004/0116949 A1   Jun. 17, 2004

Related U.S. Application Data

(60) Provisional application No. 60/433,065, filed on Dec. 11, 2002.

(51) Int. Cl.
*A61B 17/00* (2006.01)
*A61B 17/10* (2006.01)
*A61B 17/12* (2006.01)
*A61B 17/125* (2006.01)

(52) U.S. Cl. .................. 606/139; 606/153; 606/205

(58) Field of Classification Search .................. 606/153, 606/147, 148, 167, 170, 205, 206, 139, 142, 606/144
See application file for complete search history.

(56) References Cited

U.S. PATENT DOCUMENTS

| 2,201,610 | A | 5/1940 | Dawson, Jr. |
| 2,413,142 | A | 12/1946 | Jones |
| 3,150,379 | A | 9/1964 | Brown |
| 3,166,072 | A | 1/1965 | Sullivan, Jr. |
| 3,494,006 | A | 2/1970 | Brumlik |
| 3,551,987 | A | 1/1971 | Wilkinson |

(Continued)

FOREIGN PATENT DOCUMENTS

EP     0 480 428 A2     4/1992

(Continued)

OTHER PUBLICATIONS

Chuttani et al., "A Novel Endoscopic Full-thickness Plicator for Treatment of GERD: An Animal Model Study", *Gastrointestinal Endoscopy*, vol. 26, No. 1,( 2002), pp. 116-122.
Angiolink, The Expanding Vascular Staple [brochure], 1 page total.
Bluett et al., "Experimental Evaluation of Staple Lines in Gastric Surgery," *Arch. Surg.*, vol. 122, (Jul. 1987), pp. 772-776.
Angiolink, The Expanding Vascular Staple [brochure], 1 page total.
Bluett et al., "Experimental Evaluation of Staple Lines in Gastric Surgery," *Arch. Surg.*, vol. 122, (Jul. 1987), pp. 772-776.

(Continued)

*Primary Examiner*—Anhtuan T Nguyen
*Assistant Examiner*—Amy T Lang
(74) *Attorney, Agent, or Firm*—Levine Bagade Han LLP; Charles C. Fowler (57) ABSTRACT

Apparatus and methods are provided for forming a gastrointestinal tissue fold by engaging tissue at a first tissue contact point, moving the first tissue contact point from a position initially distal to a second tissue contact point to a position proximal of the second contact point to form a tissue fold, and extending an anchor assembly through the tissue fold near the second tissue contact point.

5 Claims, 8 Drawing Sheets

U.S. PATENT DOCUMENTS

| | | |
|---|---|---|
| 3,646,615 A | 3/1972 | Ness |
| 3,664,345 A | 5/1972 | Dabbs et al. |
| 3,753,438 A | 8/1973 | Wood et al. |
| 3,867,944 A | 2/1975 | Samuels |
| 3,874,388 A | 4/1975 | King et al. |
| 3,910,281 A | 10/1975 | Kletschka et al. |
| 3,976,079 A | 8/1976 | Samuels et al. |
| 4,007,743 A | 2/1977 | Blake |
| 4,060,089 A | 11/1977 | Noiles |
| 4,069,825 A | 1/1978 | Akiyama |
| 4,235,238 A | 11/1980 | Ogiu et al. |
| 4,245,624 A | 1/1981 | Komiya |
| 4,367,746 A | 1/1983 | Derechinsky |
| 4,414,720 A | 11/1983 | Crooms |
| 4,462,402 A | 7/1984 | Burgio |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,503 A | 5/1986 | Kirsch et al. |
| 4,592,339 A | 6/1986 | Kuzmak et al. |
| 4,592,356 A | 6/1986 | Gutierrez |
| 4,595,007 A | 6/1986 | Mericle |
| 4,610,250 A | 9/1986 | Green |
| 4,669,473 A | 6/1987 | Richards et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs et al. |
| 4,765,335 A | 8/1988 | Schmidt et al. |
| 4,832,055 A | 5/1989 | Palestrant |
| 4,841,888 A | 6/1989 | Mills et al. |
| 4,873,976 A | 10/1989 | Schreiber |
| 4,890,615 A | 1/1990 | Caspari et al. |
| 4,923,461 A | 5/1990 | Caspari et al. |
| 4,929,240 A | 5/1990 | Kirsch et al. |
| 4,957,498 A | 9/1990 | Caspari et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,073,166 A | 12/1991 | Parks et al. |
| 5,088,979 A | 2/1992 | Filipi et al. |
| 5,100,418 A | 3/1992 | Yoon et al. |
| 5,108,420 A | 4/1992 | Marks |
| 5,122,136 A | 6/1992 | Guglielmi et al. |
| 5,123,914 A | 6/1992 | Cope |
| RE34,021 E | 8/1992 | Mueller et al. |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,250,053 A | 10/1993 | Snyder |
| 5,254,126 A | 10/1993 | Filipi et al. |
| 5,261,916 A | 11/1993 | Engelson |
| 5,268,001 A | 12/1993 | Nicholson et al. |
| 5,282,827 A | 2/1994 | Kensey et al. |
| 5,284,488 A | 2/1994 | Sideris |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,327,914 A | 7/1994 | Shlain |
| 5,330,503 A | 7/1994 | Yoon |
| 5,334,217 A | 8/1994 | Das |
| 5,342,376 A | 8/1994 | Ruff |
| 5,345,949 A | 9/1994 | Shlain |
| 5,354,298 A | 10/1994 | Lee et al. |
| 5,366,459 A | 11/1994 | Yoon |
| 5,366,479 A | 11/1994 | McGarry et al. |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,395,030 A | 3/1995 | Kuramoto et al. |
| 5,403,326 A | 4/1995 | Harrison et al. |
| 5,403,329 A | 4/1995 | Hinchcliffe |
| 5,417,691 A | 5/1995 | Hayhurst et al. |
| 5,417,699 A | 5/1995 | Klein et al. |
| 5,425,744 A | 6/1995 | Fagan et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,680 A | 8/1995 | Yoon |
| 5,437,681 A | 8/1995 | Meade et al. |
| 5,445,167 A | 8/1995 | Yoon et al. |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,540,704 A | 7/1996 | Gordon et al. |
| 5,549,621 A | 8/1996 | Bessler et al. |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,116 A | 11/1996 | Bolanos et al. |
| 5,571,119 A | 11/1996 | Atala |
| 5,573,540 A | 11/1996 | Yoon |
| 5,573,548 A | 11/1996 | Nazre et al. |
| 5,578,045 A | 11/1996 | Das |
| 5,582,616 A | 12/1996 | Bolduc et al. |
| 5,584,835 A | 12/1996 | Greenfield |
| 5,584,859 A | 12/1996 | Brotz |
| 5,601,557 A | 2/1997 | Hayhurst |
| 5,603,718 A | 2/1997 | Xu |
| 5,613,974 A | 3/1997 | Andreas et al. |
| 5,613,975 A | 3/1997 | Christy |
| 5,626,588 A | 5/1997 | Sauer et al. |
| 5,626,614 A | 5/1997 | Hart |
| 5,630,540 A | 5/1997 | Blewett |
| 5,632,752 A | 5/1997 | Buelna |
| 5,643,274 A | 7/1997 | Sander et al. |
| 5,643,295 A | 7/1997 | Yoon |
| 5,643,317 A | 7/1997 | Pavcnik et al. |
| 5,643,320 A | 7/1997 | Lower et al. |

| | | | | | |
|---|---|---|---|---|---|
| 5,658,312 A | 8/1997 | Green et al. | 5,964,782 A | 10/1999 | Lafontaine et al. |
| 5,658,313 A | 8/1997 | Thal | 5,964,783 A | 10/1999 | Grafton et al. |
| 5,662,662 A | 9/1997 | Bishop et al. | 5,976,127 A | 11/1999 | Lax |
| 5,662,663 A | 9/1997 | Shallman | 5,976,158 A | 11/1999 | Adams et al. |
| 5,665,109 A | 9/1997 | Yoon | 5,976,159 A | 11/1999 | Bolduc et al. |
| 5,665,112 A | 9/1997 | Thal | 5,980,558 A | 11/1999 | Wiley |
| 5,667,513 A | 9/1997 | Torrie et al. | 5,984,933 A | 11/1999 | Yoon |
| 5,679,005 A | 10/1997 | Einstein | 5,993,476 A | 11/1999 | Groiso |
| 5,683,417 A | 11/1997 | Cooper | 6,013,083 A | 1/2000 | Bennett |
| 5,683,419 A | 11/1997 | Thal | 6,017,358 A | 1/2000 | Yoon et al. |
| 5,690,655 A | 11/1997 | Hart et al. | 6,027,523 A | 2/2000 | Schmieding |
| 5,693,060 A | 12/1997 | Martin | 6,033,430 A | 3/2000 | Bonutti |
| 5,700,273 A | 12/1997 | Buelna et al. | 6,045,497 A | 4/2000 | Schweich, Jr. et al. |
| 5,702,421 A | 12/1997 | Schneidt | 6,045,573 A | 4/2000 | Wenstrom, Jr. et al. |
| 5,707,394 A | 1/1998 | Miller et al. | 6,050,936 A | 4/2000 | Schweich, Jr. et al. |
| 5,709,708 A | 1/1998 | Thal | 6,053,935 A | 4/2000 | Brenneman et al. |
| 5,713,903 A | 2/1998 | Sander et al. | 6,056,770 A | 5/2000 | Epstein et al. |
| 5,720,765 A | 2/1998 | Thal | 6,059,715 A | 5/2000 | Schweich, Jr. et al. |
| 5,724,978 A | 3/1998 | Tenhoff | 6,059,719 A | 5/2000 | Yamamoto et al. |
| 5,725,552 A | 3/1998 | Kotula et al. | 6,074,401 A | 6/2000 | Gardiner et al. |
| 5,732,707 A | 3/1998 | Widder et al. | 6,077,214 A | 6/2000 | Mortier et al. |
| 5,741,297 A | 4/1998 | Simon | 6,077,281 A | 6/2000 | Das |
| 5,749,893 A | 5/1998 | Vidal et al. | 6,077,291 A | 6/2000 | Das |
| 5,752,963 A | 5/1998 | Allard et al. | 6,079,414 A | 6/2000 | Roth et al. |
| 5,766,189 A | 6/1998 | Matsuno | 6,086,600 A | 7/2000 | Kortenbach |
| 5,779,719 A | 7/1998 | Klein et al. | 6,086,601 A | 7/2000 | Yoon |
| 5,782,859 A | 7/1998 | Nicholas et al. | 6,110,183 A | 8/2000 | Cope |
| 5,782,865 A | 7/1998 | Grotz | 6,113,609 A | 9/2000 | Adams |
| 5,787,897 A | 8/1998 | Kieturakis | 6,113,611 A | 9/2000 | Allen et al. |
| 5,792,152 A | 8/1998 | Klein et al. | 6,119,913 A | 9/2000 | Adams et al. |
| 5,792,153 A | 8/1998 | Swain et al. | 6,149,658 A | 11/2000 | Gardiner et al. |
| 5,797,929 A | 8/1998 | Andreas et al. | 6,152,935 A | 11/2000 | Kammerer et al. |
| 5,797,960 A | 8/1998 | Stevens et al. | 6,159,146 A | 12/2000 | El Gazayerli |
| 5,810,849 A | 9/1998 | Kontos | 6,162,168 A | 12/2000 | Schweich, Jr. et al. |
| 5,810,851 A | 9/1998 | Yoon | 6,165,119 A | 12/2000 | Schweich, Jr. et al. |
| 5,810,853 A | 9/1998 | Yoon | 6,165,120 A | 12/2000 | Schweich, Jr. et al. |
| 5,814,064 A | 9/1998 | Daniel et al. | 6,167,889 B1 | 1/2001 | Benetti |
| 5,814,070 A | 9/1998 | Borzone et al. | 6,171,320 B1 | 1/2001 | Monassevitch |
| 5,817,110 A | 10/1998 | Kronner | 6,174,323 B1 | 1/2001 | Biggs et al. |
| 5,823,956 A | 10/1998 | Roth et al. | 6,179,195 B1 | 1/2001 | Adams et al. |
| 5,824,011 A | 10/1998 | Stone et al. | 6,183,411 B1 | 2/2001 | Mortier et al. |
| 5,827,298 A | 10/1998 | Hart et al. | RE37,117 E | 3/2001 | Palermo |
| 5,829,447 A | 11/1998 | Stevens et al. | 6,197,022 B1 | 3/2001 | Baker |
| 5,836,955 A | 11/1998 | Buelna et al. | 6,214,007 B1 | 4/2001 | Anderson |
| 5,840,078 A | 11/1998 | Yerys | 6,231,561 B1 | 5/2001 | Frazier et al. |
| 5,843,084 A | 12/1998 | Hart et al. | 6,238,412 B1 | 5/2001 | Dubrul et al. |
| 5,843,126 A | 12/1998 | Jameel | 6,245,079 B1 | 6/2001 | Nobles et al. |
| 5,846,261 A | 12/1998 | Kotula et al. | 6,260,552 B1 | 7/2001 | Mortier et al. |
| 5,855,614 A | 1/1999 | Stevens et al. | 6,261,222 B1 | 7/2001 | Schweich, Jr. et al. |
| 5,860,991 A | 1/1999 | Klein et al. | 6,264,602 B1 | 7/2001 | Mortier et al. |
| 5,861,003 A | 1/1999 | Latson et al. | 6,270,515 B1 | 8/2001 | Linden et al. |
| 5,868,762 A | 2/1999 | Cragg et al. | 6,283,973 B1 | 9/2001 | Hubbard et al. |
| 5,879,371 A | 3/1999 | Gardiner et al. | 6,290,674 B1 | 9/2001 | Roue et al. |
| 5,887,594 A | 3/1999 | LoCicero, III | 6,293,956 B1 | 9/2001 | Crainich et al. |
| 5,888,247 A | 3/1999 | Benetti | 6,296,656 B1 | 10/2001 | Bolduc et al. |
| 5,891,168 A | 4/1999 | Thal | 6,306,159 B1 | 10/2001 | Schwartz et al. |
| 5,893,856 A | 4/1999 | Jacobs et al. | 6,306,163 B1 | 10/2001 | Fitz |
| 5,895,404 A | 4/1999 | Ruiz | 6,312,437 B1 | 11/2001 | Kortenbach |
| 5,897,562 A | 4/1999 | Bolanos et al. | 6,315,789 B1 | 11/2001 | Cragg |
| 5,899,920 A | 5/1999 | DeSatnick et al. | 6,322,563 B1 | 11/2001 | Cummings et al. |
| 5,899,921 A | 5/1999 | Caspari et al. | 6,322,580 B1 | 11/2001 | Kanner |
| 5,901,895 A | 5/1999 | Heaton et al. | 6,332,468 B1 | 12/2001 | Benetti |
| 5,916,224 A | 6/1999 | Esplin | 6,332,863 B1 | 12/2001 | Schweich, Jr. et al. |
| 5,925,059 A | 7/1999 | Palermo et al. | 6,332,864 B1 | 12/2001 | Schweich, Jr. et al. |
| 5,928,264 A | 7/1999 | Sugarbaker et al. | 6,332,893 B1 | 12/2001 | Mortier et al. |
| 5,944,738 A | 8/1999 | Amplatz et al. | 6,336,940 B1 | 1/2002 | Graf et al. |
| 5,947,983 A | 9/1999 | Solar et al. | 6,346,074 B1 | 2/2002 | Roth |
| 5,947,997 A | 9/1999 | Pavcnik et al. | 6,348,064 B1 | 2/2002 | Kanner |
| 5,948,001 A | 9/1999 | Larsen | 6,355,052 B1 | 3/2002 | Neuss et al. |
| 5,954,731 A | 9/1999 | Yoon | 6,358,197 B1 | 3/2002 | Silverman et al. |
| 5,954,732 A | 9/1999 | Hart et al. | 6,363,938 B2 | 4/2002 | Saadat et al. |
| 5,961,440 A | 10/1999 | Schweich, Jr. et al. | 6,368,339 B1 | 4/2002 | Amplatz et al. |
| 5,964,765 A | 10/1999 | Fenton, Jr. et al. | 6,387,104 B1 | 5/2002 | Pugsley, Jr. |

| | | | | | | |
|---|---|---|---|---|---|---|
| 6,391,044 B1 | 5/2002 | Yadav et al. | | 2004/0030347 A1 | 2/2004 | Gannoe et al. |
| 6,402,679 B1 | 6/2002 | Mortier et al. | | 2004/0049095 A1 | 3/2004 | Goto et al. |
| 6,402,680 B2 | 6/2002 | Mortier et al. | | 2004/0059346 A1 | 3/2004 | Adams et al. |
| 6,406,420 B1 | 6/2002 | McCarthy et al. | | 2004/0082963 A1 | 4/2004 | Gannoe et al. |
| H2037 H | 7/2002 | Yates et al. | | 2004/0088008 A1 | 5/2004 | Gannoe et al. |
| 6,423,087 B1 | 7/2002 | Sawada | | 2004/0092974 A1 | 5/2004 | Gannoe et al. |
| 6,425,911 B1 | 7/2002 | Akerfeldt et al. | | 2004/0093091 A1 | 5/2004 | Gannoe et al. |
| 6,447,533 B1 | 9/2002 | Adams et al. | | 2004/0122452 A1 | 6/2004 | Deem et al. |
| 6,494,888 B1 | 12/2002 | Laufer et al. | | 2004/0122453 A1 | 6/2004 | Deem et al. |
| 6,506,196 B1 | 1/2003 | Laufer | | 2004/0122474 A1 | 6/2004 | Gellman et al. |
| 6,533,796 B1 | 3/2003 | Sauer et al. | | 2004/0138682 A1 | 7/2004 | Onuki et al. |
| 6,537,285 B1 | 3/2003 | Hatasaka, Jr. et al. | | 2004/0147941 A1 | 7/2004 | Takemoto |
| 6,554,845 B1 | 4/2003 | Fleenor et al. | | 2004/0176784 A1 | 9/2004 | Okada |
| 6,558,400 B2 | 5/2003 | Deem et al. | | 2004/0193117 A1 | 9/2004 | Laufer et al. |
| 6,572,629 B2 | 6/2003 | Kalloo et al. | | 2004/0193184 A1 | 9/2004 | Laufer et al. |
| 6,641,592 B1 | 11/2003 | Sauer et al. | | 2004/0193193 A1 | 9/2004 | Laufer et al. |
| 6,656,194 B1 | 12/2003 | Gannoe et al. | | 2004/0193194 A1 | 9/2004 | Laufer et al. |
| 6,663,639 B1 | 12/2003 | Laufer et al. | | 2004/0194790 A1 | 10/2004 | Laufer et al. |
| 6,695,764 B2 | 2/2004 | Silverman et al. | | 2004/0215216 A1 | 10/2004 | Gannoe et al. |
| 6,716,232 B1 | 4/2004 | Vidal et al. | | 2004/0243152 A1 | 12/2004 | Taylor et al. |
| 6,719,763 B2 | 4/2004 | Chung et al. | | 2004/0249362 A1 | 12/2004 | Levine et al. |
| 6,719,764 B1 | 4/2004 | Gellman et al. | | 2004/0249392 A1 | 12/2004 | Mikkaichi et al. |
| 6,736,828 B1 | 5/2004 | Adams et al. | | 2004/0249395 A1 | 12/2004 | Mikkaichi et al. |
| 6,746,460 B2 | 6/2004 | Gannoe et al. | | 2005/0033320 A1 | 2/2005 | McGuckin, Jr. et al. |
| 6,755,843 B2 | 6/2004 | Chung et al. | | 2005/0033328 A1 | 2/2005 | Laufer et al. |
| 6,773,440 B2 | 8/2004 | Gannoe et al. | | 2005/0043758 A1 | 2/2005 | Golden et al. |
| 6,773,441 B1 | 8/2004 | Laufer et al. | | 2005/0049617 A1 | 3/2005 | Chatlynne et al. |
| 6,821,285 B2 * | 11/2004 | Laufer et al. ............ 606/153 | | 2006/0241661 A1 * | 10/2006 | DeVries et al. ............ 606/153 |
| 6,835,199 B2 | 12/2004 | McGuckin, Jr. et al. | | | | |

FOREIGN PATENT DOCUMENTS

| | | | |
|---|---|---|---|
| 2001/0016675 A1 | 8/2001 | Mortier et al. | |
| 2001/0025171 A1 | 9/2001 | Mortier et al. | |
| 2001/0049509 A1 | 12/2001 | Sekine et al. | |
| 2001/0051815 A1 | 12/2001 | Esplin | |
| 2001/0056282 A1 | 12/2001 | Sonnenschein et al. | |
| 2002/0010490 A1 | 1/2002 | Schaller et al. | |
| 2002/0013608 A1 | 1/2002 | ElAttrache et al. | |
| 2002/0019649 A1 | 2/2002 | Sikora et al. | |
| 2002/0022851 A1 | 2/2002 | Kalloo et al. | |
| 2002/0029080 A1 | 3/2002 | Mortier et al. | |
| 2002/0040226 A1 | 4/2002 | Laufer et al. | |
| 2002/0055757 A1 | 5/2002 | Torre et al. | |
| 2002/0058855 A1 | 5/2002 | Schweich, Jr. et al. | |
| 2002/0065534 A1 | 5/2002 | Hermann et al. | |
| 2002/0068849 A1 | 6/2002 | Schweich, Jr. et al. | |
| 2002/0068945 A1 | 6/2002 | Sixto, Jr. et al. | |
| 2002/0072761 A1 | 6/2002 | Abrams et al. | |
| 2002/0077524 A1 | 6/2002 | Schweich, Jr. et al. | |
| 2002/0078967 A1 | 6/2002 | Sixto, Jr. et al. | |
| 2002/0082621 A1 | 6/2002 | Schurr et al. | |
| 2002/0082622 A1 | 6/2002 | Kane | |
| 2002/0107530 A1 | 8/2002 | Sauer et al. | |
| 2002/0111534 A1 * | 8/2002 | Suzuki et al. ............ 600/102 | |
| 2002/0183768 A1 | 12/2002 | Deem et al. | |
| 2002/0193816 A1 | 12/2002 | Laufer et al. | |
| 2003/0009085 A1 | 1/2003 | Arai et al. | |
| 2003/0055442 A1 | 3/2003 | Laufer et al. | |
| 2003/0065359 A1 | 4/2003 | Weller et al. | |
| 2003/0109892 A1 | 6/2003 | Deem et al. | |
| 2003/0139752 A1 | 7/2003 | Pasricha et al. | |
| 2003/0158582 A1 | 8/2003 | Bonutti et al. | |
| 2003/0167062 A1 | 9/2003 | Gambale et al. | |
| 2003/0171651 A1 | 9/2003 | Page et al. | |
| 2003/0171760 A1 | 9/2003 | Gambale | |
| 2003/0176890 A1 | 9/2003 | Buckman et al. | |
| 2003/0181924 A1 | 9/2003 | Yamamoto et al. | |
| 2003/0204205 A1 | 10/2003 | Sauer et al. | |
| 2003/0240205 | 10/2003 | Sauer at al. | |
| 2003/0208209 A1 | 11/2003 | Gambale et al. | |
| 2003/0216613 A1 | 11/2003 | Suzuki et al. | |
| 2003/0225312 A1 | 12/2003 | Suzuki et al. | |
| 2003/0229296 A1 | 12/2003 | Ishikawa et al. | |
| 2003/0236536 A1 | 12/2003 | Grigoryants et al. | |
| 2004/0010271 A1 | 1/2004 | Kortenbach | |

| | | |
|---|---|---|
| EP | 0 847 727 A1 | 6/1998 |
| EP | 1 031 321 A1 | 8/2000 |
| FR | 2 768 324 A1 | 3/1999 |
| GB | 2 165 559 A | 4/1986 |
| WO | WO 92/04870 A1 | 4/1992 |
| WO | WO 95/19140 A1 | 7/1995 |
| WO | WO 95/25468 A1 | 9/1995 |
| WO | WO 99/22649 A2 | 5/1999 |
| WO | WO 00/40159 A1 | 7/2000 |
| WO | WO 00/57796 A1 | 10/2000 |
| WO | WO 00/78227 A1 | 12/2000 |
| WO | WO 00/78229 A1 | 12/2000 |
| WO | WO 01/21246 A1 | 3/2001 |
| WO | WO 01/66001 A2 | 9/2001 |
| WO | WO 01/66018 A1 | 9/2001 |
| WO | WO 01/85034 A1 | 11/2001 |
| WO | WO 01/87144 A1 | 11/2001 |
| WO | WO 01/89370 A2 | 11/2001 |
| WO | WO 01/89392 A2 | 11/2001 |
| WO | WO 01/89393 A1 | 11/2001 |
| WO | WO 02/00119 A2 | 1/2002 |
| WO | WO 02/24080 A2 | 3/2002 |
| WO | WO 02/39880 A2 | 5/2002 |
| WO | WO 02/060328 A1 | 8/2002 |
| WO | WO 02/064012 A2 | 8/2002 |
| WO | WO 02/085252 A1 | 10/2002 |
| WO | WO 02/094105 A2 | 11/2002 |
| WO | WO 03/007796 A2 | 1/2003 |
| WO | WO 03/007799 A2 | 1/2003 |
| WO | WO 03/090633 A2 | 11/2003 |
| WO | WO 03/092509 A1 | 11/2003 |
| WO | WO 03/094785 A1 | 11/2003 |
| WO | WO 03/096909 A1 | 11/2003 |
| WO | WO 03/099137 A2 | 12/2003 |
| WO | WO 2004/004542 A2 | 1/2004 |
| WO | WO 2004/004544 A2 | 1/2004 |
| WO | WO 2004/019787 A2 | 3/2004 |
| WO | WO 2004/019788 A2 | 3/2004 |
| WO | WO 2004/021865 A2 | 3/2004 |
| WO | WO 2004/021867 A2 | 3/2004 |
| WO | WO 2004/021868 A2 | 3/2004 |
| WO | WO 2004/021873 A2 | 3/2004 |

| WO | WO 2004/021894 A1 | 3/2004 |
| WO | WO 2004/056273 A1 | 7/2004 |
| WO | WO 2004/075787 A1 | 9/2004 |
| WO | WO 2005/004727 A1 | 1/2005 |
| WO | WO 2005/037152 A1 | 4/2005 |

OTHER PUBLICATIONS

Brolin et al., Experimental Evaluation of Techniques of Gastric Paritioning for Morbid Obesity, Surgery, Gynecology & Obstetrics, vol. 153, (Dec. 1981), pp. 878-882.

Johnston et al. "The Magenstrasse and Mill Operation of Morbid Obesity", *Obesity Surgery* 13, (2003), pp. 10-16.

Okudaira et al., "The Healing and Tensile Strength of the Gastroplasty Staple Line," *The American Surgeon*, (Oct. 1984), pp. 564-568.

Surgical Dynamics Inc., The S•D•sorb Meniscal Stapler [brochure] (1997), 3 pages total.

Sutura, The Next Generation in Vascular Suturing Devices: SuperStitch [brochure], 2 pages total.

\* cited by examiner

APPARATUS AND METHODS FOR FORMING GASTROINTESTINAL TISSUE APPROXIMATIONS

REFERENCE TO RELATED APPLICATIONS

This application claims priority from U.S. Provisional Patent Application No. 60/433,065, filed Dec. 11, 2002, which is incorporated herein by reference in its entirety.

FIELD OF THE INVENTION

The present invention relates to methods and apparatus for reducing the effective cross-sectional area of a gastro-intestinal ("GI") lumen.

BACKGROUND OF THE INVENTION

The onset of minimally invasive surgery, laparoscopy, has significantly reduced the morbidity for patients and decreased costs for surgery. The next frontier in less invasive surgery is to perform these procedures using the natural passageways of the GI tract. There are numerous gastrointestinal indications that could benefit from an endoluminal approach. These indications include GERD, gastric resections, transluminal procedures, revision of gastric bypass procedures, anastomosis for gastric bypass, gastroplasty, colonic resections, large polyps, and transanal microsurgery.

Morbid obesity is a serious medical condition pervasive in the United States and other industrialized countries. Its complications include hypertension, diabetes, coronary artery disease, stroke, congestive heart failure, multiple orthopedic problems and pulmonary insufficiency with markedly decreased life expectancy.

Several surgical techniques have been developed to treat morbid obesity, e.g., bypassing an absorptive surface of the small intestine, or reducing the stomach size. These procedures are difficult to perform in morbidly obese patients because it is often difficult to gain access to the digestive organs. In particular, the layers of fat encountered in morbidly obese patients make difficult direct exposure of the digestive organs with a wound retractor, and standard laparoscopic trocars may be of inadequate length.

In addition, previously known open surgical procedures may present numerous life-threatening post-operative complications, and may cause atypical diarrhea, electrolytic imbalance, unpredictable weight loss and reflux of nutritious chyme proximal to the site of the anastomosis.

The gastrointestinal lumen includes four tissue layers, wherein the mucosa layer is the top tissue layer followed by connective tissue, the muscularis layer and the serosa layer. When stapling or suturing from the peritoneal side of the GI tract, it is easier to gain access to the serosal layer. In endoluminal approaches to surgery, the mucosa layers are visualized. The muscularis and serosal layers are difficult to access because they are only loosely adhered to the mucosal layer. In order to create a durable tissue approximation with suture or staples or some form of anchor, it is important to create a serosa to serosa approximation. In other words, the mucosa and connective tissue layers typically do not heal together in a way that can sustain the tensile loads imposed by normal movement of the stomach wall during ingestion and processing of food. In particular, folding the serosal layers in a way that they will heal together will form a durable plication. This problem of capturing the muscularis or serosa layers becomes particularly acute where it is desired to place an anchor or other apparatus transesophageally rather than intraoperatively, since care must be taken in piercing the tough stomach wall not to inadvertently puncture adjacent tissue or organs.

In view of the aforementioned limitations, it would be desirable to provide methods and apparatus for folding serosal layers and plicating them to heal together. This can be used to achieve gastric reduction by reconfiguring the GI lumen of a patient as well as stopping bleeding in the GI tract and resecting lesions from the inside of the gastrointestinal lumens.

It also would be desirable to provide methods and apparatus for gastric reduction wherein an anchor assembly is extended across stomach folds that include the muscularis and serosa tissue layers, thereby providing a durable foundation for placement of gastric reduction apparatus.

It further would be desirable to provide methods and apparatus for gastric reduction, wherein the anchors are deployed in a manner that reduces the possibility of injuring neighboring organs.

SUMMARY OF THE INVENTION

In view of the foregoing, it is an object of the present invention to provide methods and apparatus for achieving a serosa-to-serosa approximation endoluminally.

It is another object of the present invention to provide methods and apparatus for gastric reduction by reconfiguring the GI lumen of a patient, by creating a restriction to the passage of food.

It is another object of the present invention to provide methods and apparatus for gastric reduction using anchors that can be reconfigured from a reduced delivery profile to an expanded deployed profile.

It is an additional object of this invention to provide methods and apparatus for gastric reduction in which an anchor assembly is extended across stomach folds that include the muscularis and serosa tissue layers, thereby providing a durable foundation for placement of gastric reduction apparatus.

It is a further object of the present invention to provide methods and apparatus for various gastrointestinal surgery including gastric reduction, wherein the anchors are deployed in a manner that reduces the possibility of injuring neighboring organs.

According to one aspect of the present invention, a gastrointestinal tissue fold is created by advancing a delivery catheter that includes first and second flexible tubes into a gastrointestinal lumen ("GI lumen"), wherein the first flexible tube has a distal tip carrying a tissue grabbing assembly. A tissue wall of the GI lumen is engaged with the tissue grabbing assembly, and then maneuvered to create a tissue fold. The second flexible tube then is positioned so that its distal tip is substantially perpendicular to the tissue fold and an anchor assembly is delivered through the second flexible tube and across the tissue fold. Preferably, delivery of the anchor assembly across the tissue fold includes delivering the anchor assembly across the muscularis and serosa layers of the tissue wall and directed back inwardly into the gastric lumen.

According to other embodiments, the tissue grabbing assembly may comprise a pair of jaws configured to transform between open and closed configurations, wherein the jaws have sharpened teeth to facilitate tissue engagement. Preferably, the flexible tubes are connected by a hinge assembly that limits movement of the first flexible tube relative to the second flexible tube.

In another aspect of the present invention, a gastrointestinal tissue fold is formed by advancing a delivery catheter including a flexible tube into a gastrointestinal lumen. The flexible tube includes a distal tip having a tissue grabbing assembly disposed thereon, which is actuated to engage the tissue wall and then move the tissue wall to create a tissue fold. The tissue grabbing assembly then is rotated to move the tissue fold across a distal bend in the flexible tube, through which an anchor assembly is delivered across the tissue fold.

According to alternative embodiments, the tissue grabbing assembly may comprise a treadmill assembly including a plurality of needles. The needles are disposed on a band at regular intervals to form a conveyor that rotates around a distal hub and a proximal hub. The proximal hub is operatively coupled to a drive shaft disposed within the flexible tube so that rotation of the drive shaft rotates the proximal hub and linearly displaces the conveyor.

According to another method of the present invention, a gastrointestinal tissue fold is formed by engaging the tissue at a first engagement point, moving the first engagement point to a position proximal of a second engagement point to form a fold, and then engaging the tissue at the second engagement point. In a preferred embodiment, the tissue is engaged at the second engagement point by extending an anchor assembly through the tissue fold using a needle.

The anchor assembly comprises, in one embodiment, a pair of anchors comprising rods that are delivered through a needle in a reduced delivery profile, wherein the longitudinal axis of the rods is substantially parallel to the longitudinal axis of the needle. Once ejected from the needle, the rods are free to rotate about 90 degrees to engage the tissue. In other embodiments, the anchor assembly comprises a pair of anchors including cylinders that are delivered using an obturator. In a reduced delivery profile, a longitudinal axis of the cylinders is substantially parallel to the longitudinal axis of the obturator. After delivery the cylinders rotate 90 degrees about their longitudinal axes to bear against the tissue.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

In accordance with the principles of the present invention, methods and apparatus are provided for treating obesity by approximating the walls of a gastrointestinal lumen to narrow the lumen, thus reducing the area for absorption in the stomach or intestines. More particularly, the present invention involves an endoscopic apparatus that engages a tissue wall of the gastrointestinal lumen, creates a tissue fold and disposes an anchor assembly through the tissue fold. Preferably, the anchor assembly is disposed through the muscularis and/or serosa layers of the gastrointestinal lumen. In operation, the distal tip of the probe engages the tissue, then moves the engaged tissue to a proximal position relative to the catheter tip, thereby providing a substantially uniform plication of predetermined size.

Formation of a tissue fold preferably is accomplished using two tissue contact points that are separated by a linear or curvilinear distance, wherein the separation distance between the tissue contact points affects the length and/or depth of the fold. In operation, a tissue grabbing assembly engages the tissue wall in its normal state (i.e., non-folded and substantially flat), thus providing a first tissue contact point. The first tissue contact point then is moved to a position proximal of a second tissue contact point to form the tissue fold. An anchor assembly then may be extended across the tissue fold at the second tissue contact point.

More preferably, the first tissue contact point is used to engage and then stretch or rotate the tissue wall over the second tissue contact point to form the tissue fold. The tissue fold is then articulated to a position so that a portion of the tissue fold overlies the second tissue contact point at an orientation that is substantially normal to the tissue fold. An anchor then is delivered across the tissue fold at or near the second tissue contact point.

Figure 1A:
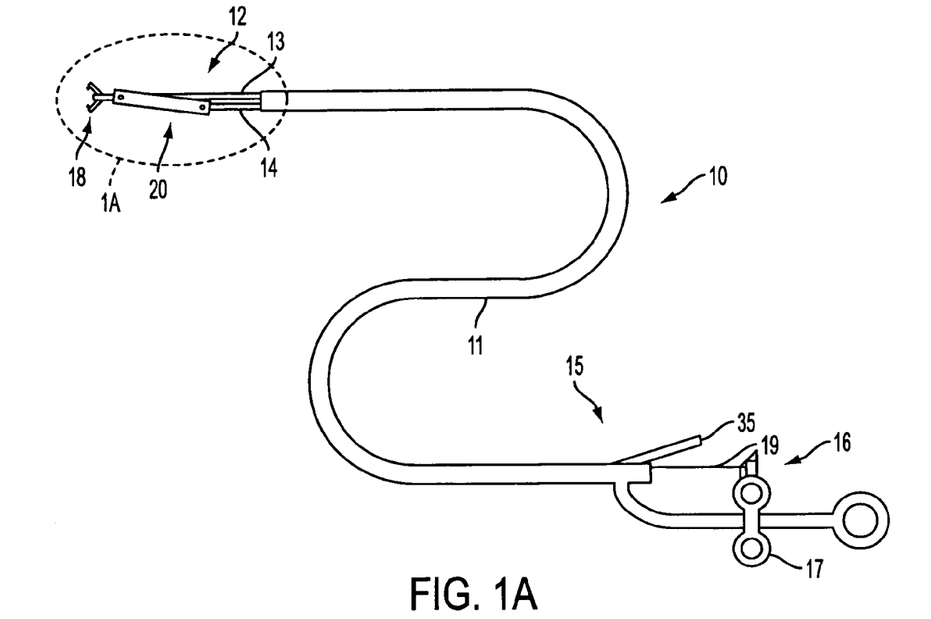
FIGS. 1A and 1B are, respectively, a side view and detailed view, of apparatus of the present invention for forming a gastrointestinal fold in accordance with the principles of the present invention.
Figure 1B:
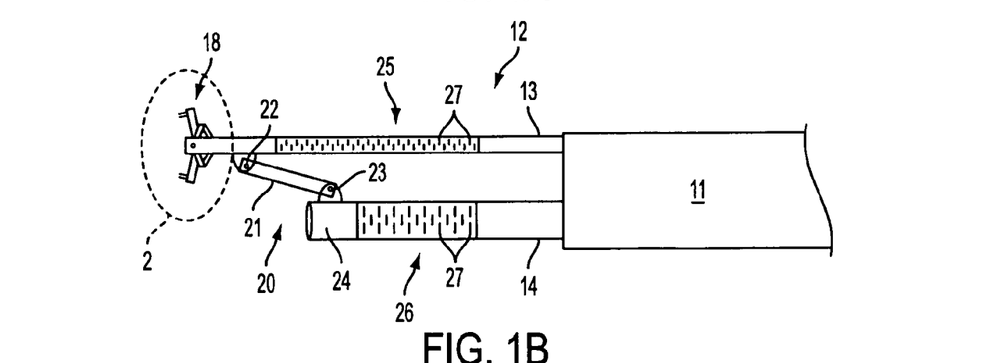

Referring to FIGS. 1A and 1B, apparatus 10 of the present invention comprises torqueable catheter 11 having distal region 12 from which first and second interconnected flexible tubes 13 and 14 extend, and proximal region 15 having handle 16 and actuator 17. Catheter 11 is configured to be inserted through a patient's mouth and esophagus and into the gastrointestinal lumen. Tissue grabbing assembly 18 is disposed on the distal end of flexible tube 13, and is coupled to actuator 17 via control wire 19 that extends through flexible tube 13.

As better illustrated in FIG. 1B, flexible tubes 13 and 14 are connected via hinge assembly 20 that comprises link 21 attached to flexible tube 13 at pivot point 22 and attached to flexible tube 14 at pivot point 23. Hinge assembly 20 prevents tissue grabbing assembly 18 from moving more than a predetermined distance relative to distal end 24 of flexible tube 14.

Still referring to FIG. 1B, flexible tubes 13 and 14 preferably include bendable sections 25 and 26, respectively, that comprise a plurality of through-wall slots 27 to enhance flexibility of the tube. Preferably, flexible tubes 13 and 14 are made from stainless steel with an etched or laser-cut slot pattern. More preferably, the slot pattern is a sinusoidal repeating pattern of slots perpendicular to the longitudinal axis of tubes 13 and 14.

Figure 2A:
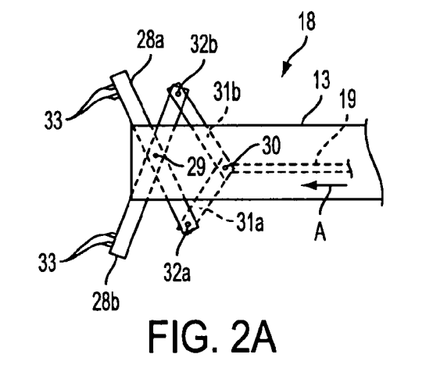
FIGS. 2A and 2B are side-sectional views of a tissue grabbing assembly suitable for use with the apparatus of FIG. 1.
Figure 2B:
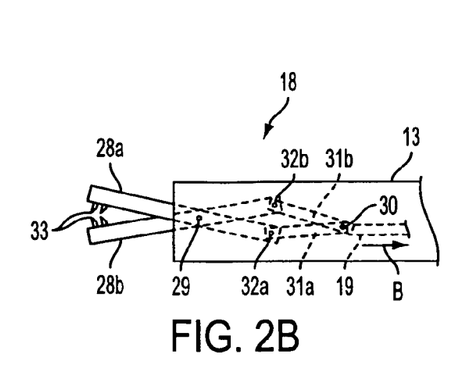

Referring to FIGS. 2A and 2B, tissue grabbing assembly 18 comprises pair of jaws 28a, 28b arranged to rotate about pivot point 29 between an open configuration (FIG. 2A) and a closed configuration (FIG. 2B). Control wire 19 is coupled via pivot point 30 to arms 31*a* and 31*b*. Arms 31*a* and 31*b* are in turn pivotally coupled to jaws 28*a* and 28*b*, respectively, at pivot points 32*a* and 32*b*. Each of jaws 28*a* and 28*b* preferably includes sharpened teeth 33 disposed near its distal ends to facilitate grasping of the tissue wall of the GI lumen.

Control wire 19 is coupled to actuator 17 of handle 16 so that translation of the wire within flexible tube 13 causes the jaws to open or close. In particular, urging control wire distally (as indicated by arrow A in FIG. 2A) moves pivot point 30 distally, thereby forcing the jaws to open. Urging control wire 19 proximally (as indicated by arrow B in FIG. 2B) moves pivot point 30 proximally, thereby forcing the jaws to close together. In alternative embodiments, tissue grabbing assembly 18 may comprise a grappling hook or fork, or plurality of needles coupled to the distal end of flexible tube 13.

Flexible tube 14 is affixed to and immovable within catheter 11, while flexible tube 13 is coupled to catheter 11 only via hinge 20. Accordingly, when control wire 19 is extended in the distal direction, flexible tube 13 is carried in the distal direction. When control wire 19 is retracted in the proximal direction, flexible tube remains stationary until jaws 28*a* and 28*b* close together, after which further retraction of control wire 19 by moving actuator 17 causes flexible tube to buckle in bendable region 25, as described hereinafter.

Figure 3A:
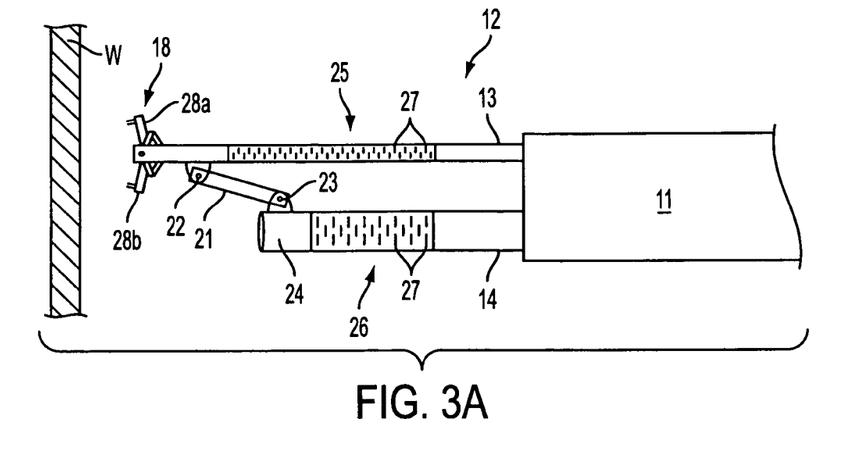
FIGS. 3A-3E depict side views of the apparatus of FIG. 1 used in forming a gastrointestinal fold in accordance with the methods of the present invention.
Figure 3B:
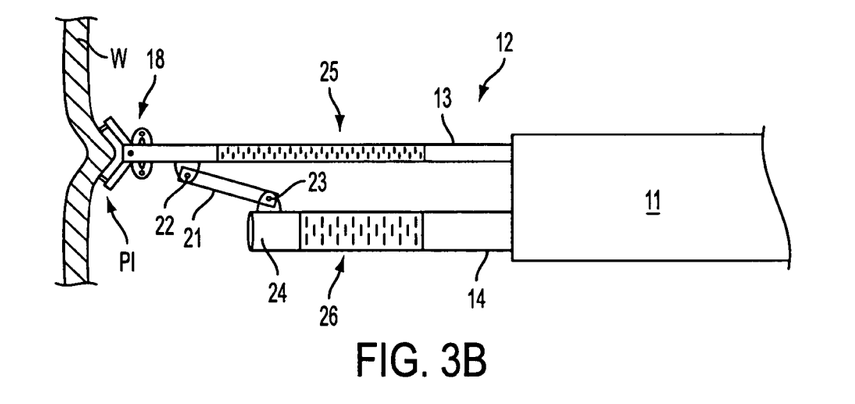

Referring now to FIGS. 1 and 3A-3E, operation of apparatus 10 is described to create a tissue fold in a tissue wall of a GI lumen. In FIG. 3A, distal region 12 of catheter 11 is positioned within a patient's GI lumen transesophageally, and jaws 28*a* and 28*b* of tissue grabbing assembly 18 are opened by moving actuator 17 to the distal-most position on handle 16. As depicted in FIG. 3B, actuator 17 may then be moved proximally until the jaws of tissue grabbing assembly 18 engage a portion of tissue wall W at contact point P1.

Figure 3C:
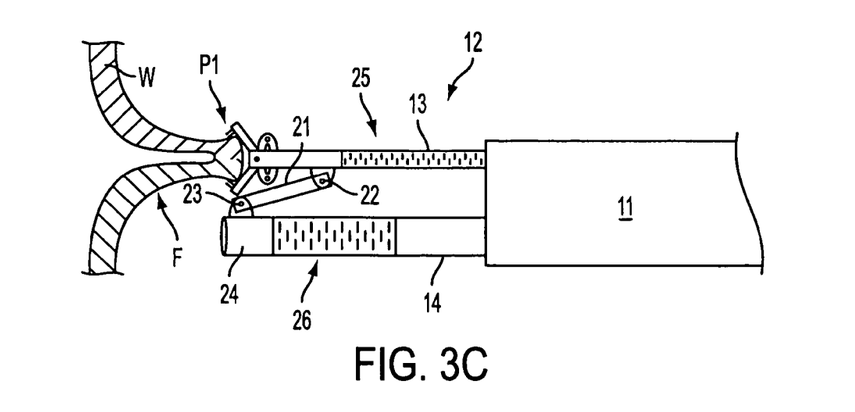

Referring to FIG. 3C, after the tissue wall has been engaged at contact point P1, flexible tube 13 is urged proximally within catheter 11 by further proximal retraction of control wire 19 to stretch tissue wall W and create tissue fold F. During this movement of flexible tube 13, link 21 of hinge assembly 20 causes tissue grabbing assembly 18 to move from a position distal to distal end 24 of flexible tube 14, to a position proximal of distal end 24 of flexible tube 14. Bendable sections 25 and 26 of flexible tubes 13 and 14, respectively, accommodate any lateral motion caused by operation of hinge assembly 20. Advantageously, formation of fold F facilitates the penetration of the tissue wall by a needle and subsequent delivery of an anchor assembly, as described hereinafter.

Figure 3D:
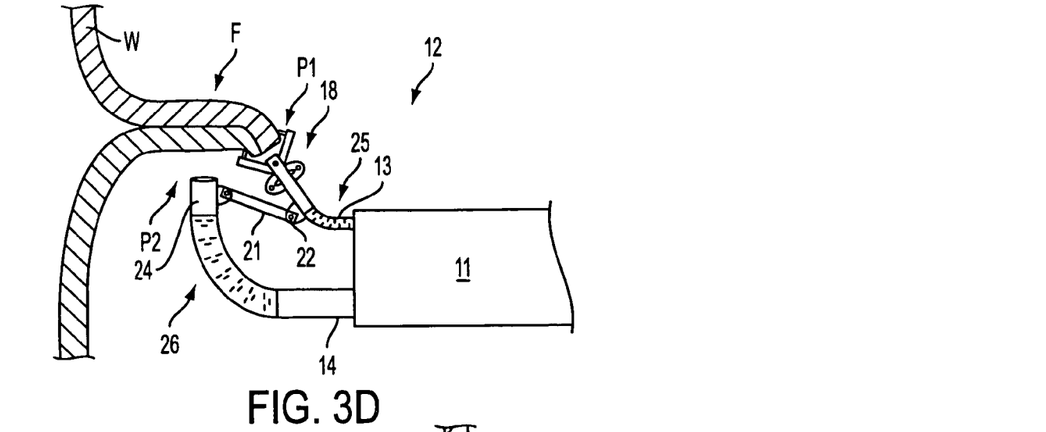
Figure 3E:
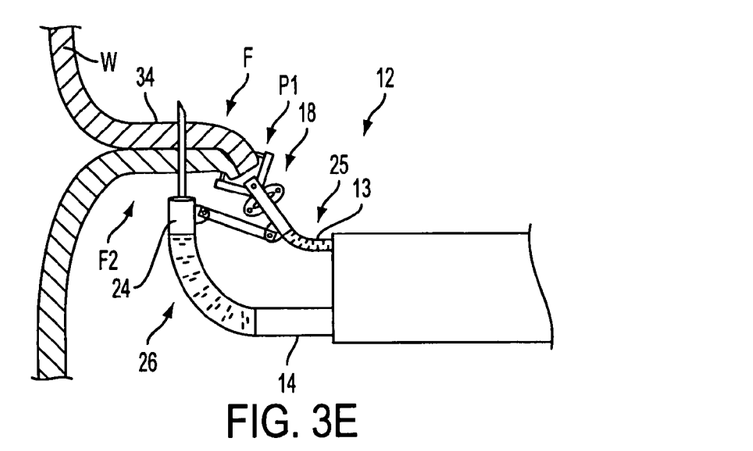

Referring to FIG. 3D, additional proximal movement of actuator 17 causes flexible tubes 13 and 14 to buckle at bendable sections 25 and 26. The force applied to flexible tube 13 via control wire 19 and actuator 17 is transmitted to the distal tip 24 of the flexible tube 14 by hinge assembly 20. Preferably, flexible tube 14 is configured so that distal tip 24 contacts, and is substantially perpendicular, to tissue fold F at contact point P2. As illustrated in FIG. 3E, once tissue fold F is stretched across distal tip 24 of flexible tube 14, sharpened needle or obturator 34 may be extended from distal tip 24 of flexible tube 14 to pierce all four layers of the tissue wall W. Sharpened needle or obturator 34 is inserted via inlet 35 to flexible tube 14 on handle 16 (see FIG. 1A).

As discussed above, the GI lumen comprises an inner mucosal layer, connective tissue, the muscularis layer and the serosa layer. To obtain a durable purchase, e.g., in performing a stomach reduction procedure, the staples or anchors used to achieve reduction of the GI lumen must engage at least the muscularis tissue layer, and more preferably, the serosa layer as well. Advantageously, stretching of tissue fold F across distal tip 24 permits an anchor to be ejected through both the muscularis and serosa layers, thus enabling durable gastrointestinal tissue approximation.

As depicted in FIG. 3E, after tissue fold F is stretched across distal tip 24 of flexible tube 14 to form contact point P2 with tissue wall W, needle 34 may be extended from distal tip 24 and through tissue fold F. Because needle 34 penetrates the tissue wall twice, it exits within the gastrointestinal lumen, thus reducing the potential for injury to surrounding organs. Once the needle has penetrated tissue fold F, an anchor assembly is ejected through distal tip 24 as described hereinbelow.

Figure 4A:
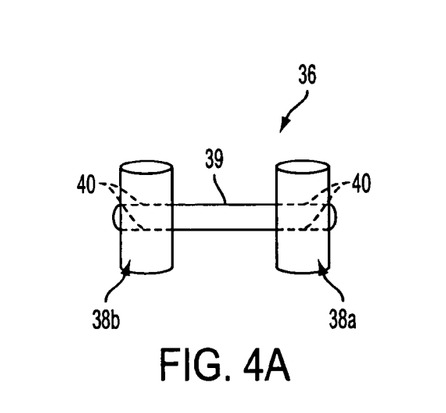
FIGS. 4A-4C are side-sectional views of an anchor assembly suitable for use with the apparatus of the present invention.
Figure 4B:
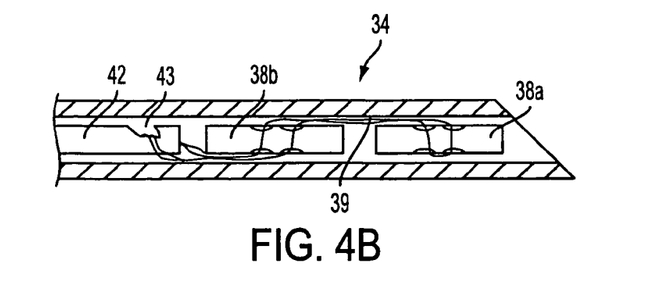
Figure 4C:
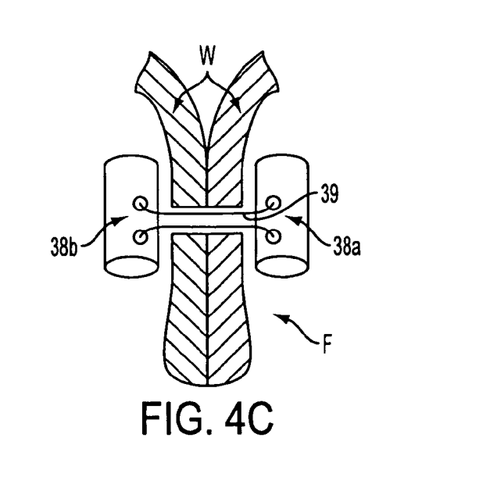

With respect to FIGS. 4A-4C, a first embodiment of an anchor assembly suitable for use with the apparatus of the present invention is described. Anchor assembly 36 comprises T-anchor assembly having distal rod 38*a* and proximal rod 38*b* connected by suture 39. The precise shape, size and materials of the anchors may vary for individual applications. In addition, the suture material also may vary for individual applications. By way of example, the suture material may consist of monofilament wire, multifilament wire or any other conventional suture material. Suture 39 extends through a pair of through holes 40 in each rod, thereby forming a loop. Alternatively, suture 39 may be attached to the rods via an eyelet or using a suitable adhesive. Preferably, through-holes 40 are located near the center of the rods 38*a* and 38*b*.

Referring to FIG. 4B, rods 38*a* and 38*b* may be delivered through needle 34 (see FIG. 3E) using push rod 42. Push rod 42 is adapted to freely translate through flexible tube 14 and needle 34. Push rod 42 is preferably flexible, so that it may slide through bendable section 26 of flexible tube 14. In addition, push rod 42 may include notch 43 near its distal end to facilitate grasping and tensioning suture 39 after anchor delivery.

During anchor delivery, the longitudinal axis of distal rod 38*a* is substantially parallel to the longitudinal axis of needle 34. However, once distal rod 38*a* is ejected from needle 34, suture tension induces the rod to rotate approximately 90 degrees about its longitudinal axis, so that its longitudinal axis is substantially perpendicular to the longitudinal axis of needle 35. This rotation of distal rod 38*a* prevents it from being pulled back through tissue wall W.

Referring to FIG. 4C, once rod 38*a* is ejected on the distal side of fold F, needle 35 is retracted and push rod 42 is used to eject rod 38*b* on the proximal side of tissue fold F. Like distal rod 38*a*, tension in the suture causes proximal rod 38*b* to rotate about 90 degrees once it is ejected from the needle. Notch 43 in push rod 42 then may be employed to tighten suture 39 by any of a variety of mechanisms.

Figure 5A:
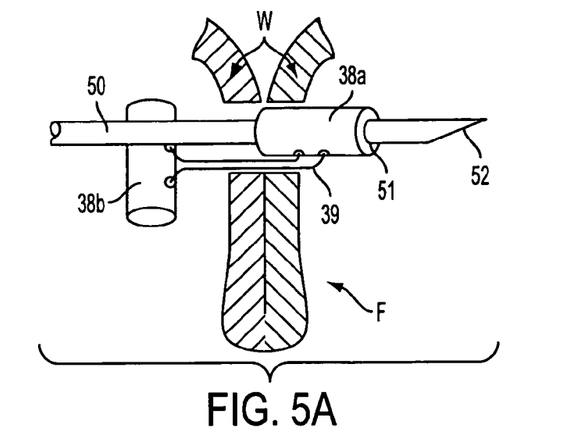
FIGS. 5A and 5B are side-sectional views of another anchor assembly suitable for use with the apparatus of the present invention.

Referring now to FIG. 5A, according to other embodiments, the anchor assembly comprises a T-anchor assembly suitable to be disposed over obturator 50. More particularly, distal rod 38*a* includes through-hole 51 dimensioned for the passage of obturator tip 52, and obturator 50 is translatably inserted through flexible tube 14 via inlet 35 of handle 16 (see FIG. 1A). Proximal rod 38*b* may be a solid rod that does not include a through-hole for passage of obturator 50. Alternatively, proximal rod 38*b* may include a through-hole for the passage of the obturator. Preferably, obturator tip 52 is sharpened to facilitate tissue penetration.

Figure 5B:
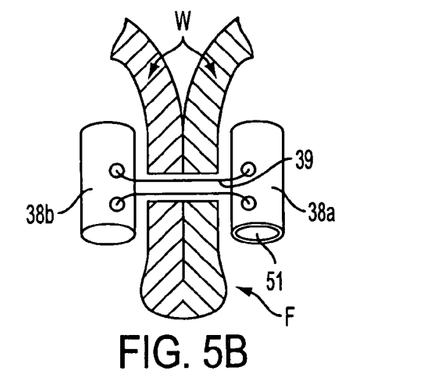

With respect to FIG. 5B, once rod 38*a* is ejected on the distal side of fold F, it rotates into a position substantially parallel to tissue wall W and perpendicular to the longitudinal axis of the obturator. Obturator 50 then is retracted and proximal rod 38*b* is ejected from flexible tube 14. More particularly, when flexible tube 14 is retracted from tissue wall W, proximal rod 38*b* is pulled through distal tip 24. Proximal rod 38b then rotates substantially 90 degrees as it is ejected from flexible tube 14 so that rod 38b is urged against tissue wall W.

Figure 6A:
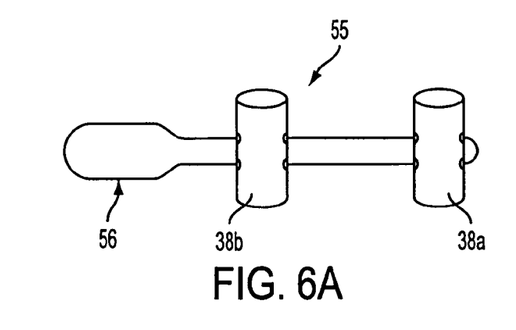
FIGS. 6A and 6B are side-sectional views of another alternative anchor assembly suitable for use with the apparatus of the present invention.

Referring to FIG. 6A, according to further embodiments, anchor assembly 55 comprises a T-anchor assembly similar to the embodiment depicted in FIG. 4A. However, anchor assembly 55 includes fine wire tether 56 that may be twisted to maintain the tension between rods 38a and 38b.

Figure 6B:
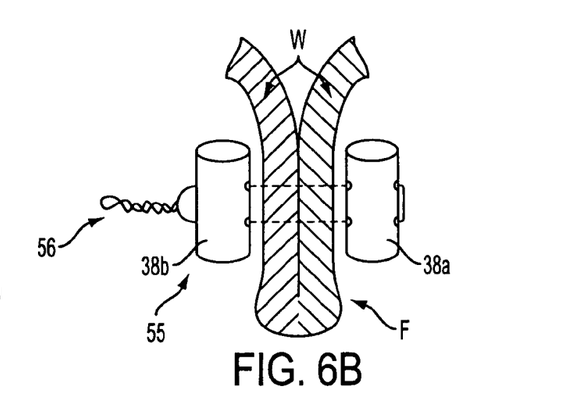

With respect to FIG. 6B, a method of delivering anchor assembly 55 is described. Initially, distal rod 38a is delivered across both tissue walls using needle 34. The needle then is retracted to release distal rod 38a so that it engages the tissue wall. Next, needle 34 is retracted to release proximal rod 38b, so that it too rotates into engagement with the tissue wall. A proximal portion of the wire tether is captured by notch 43 of push rod 42 (see FIG. 4B), and the push rod is rotated to cause proximal rod 38b to clamp down on the tissue fold. Because wire tether 56 is twisted by rotation of push rod 42, it maintains the desired force on the tissue walls.

Figure 7A:
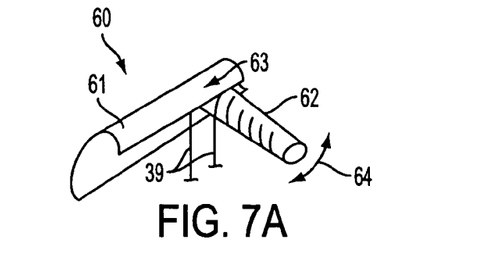
FIGS. 7A-7D are perspective views of alternative anchors suitable for use with the anchor assemblies of the present invention.

FIGS. 7A-7D depict other alternative anchor embodiments suitable for use with the methods and apparatus of the present invention. Referring to FIG. 7A, articulating anchor 60 includes semi-cylindrical base 61, rod 62 and suture 39. Rod 62 rotates about pivot point 63 (as indicated by arrow 64) between an expanded position (shown in FIG. 7A) and a reduced profile position, wherein rod 62 pivots within the semi-cylindrical base 61. Articulating anchor 60 may be delivered through a tissue fold using needle 34 described hereinabove with respect to FIG. 3E. Preferably, articulating anchor 60 is biased in the expanded position so that it automatically expands once it is ejected from the needle.

Figure 7B:
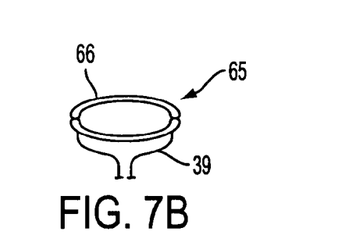
Figure 7C:
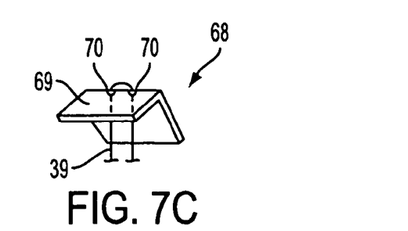
Figure 7D:
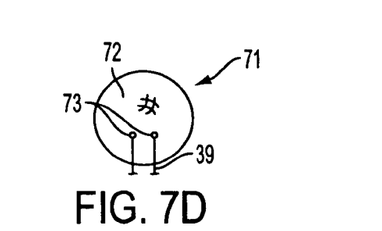

With respect to FIGS. 7B and 7C the anchors of the present invention also may comprise a pair of oblong bodies connected by at least one suture. In FIG. 7B, anchor 65 comprises elliptical ring 66 having sutures 39 attached at substantially opposite sides of the ring. In FIG. 7C, anchor 68 comprises angle bracket 69 having a pair of through-holes 70 for suture 39. In FIG. 7D, anchor 71 comprises oblong bead 72 having a pair of through-holes 73 for suture 39. All three anchors 65, 68 and 71 have a first dimension (e.g., width) that is substantially larger than a second dimension (e.g., height). This dimensional difference necessitates that anchors 65, 68 and 71 be inserted within needle (e.g., needle 34 of FIG. 3E) in a particular orientation. Once the anchor is ejected through a tissue wall, tension on suture 39 forces the anchor to rotate so that it cannot be pulled back through the tissue wall. As will be understood by those of skill in the art, numerous other anchors may be employed without departing from the scope of the present invention.

Figure 8A:
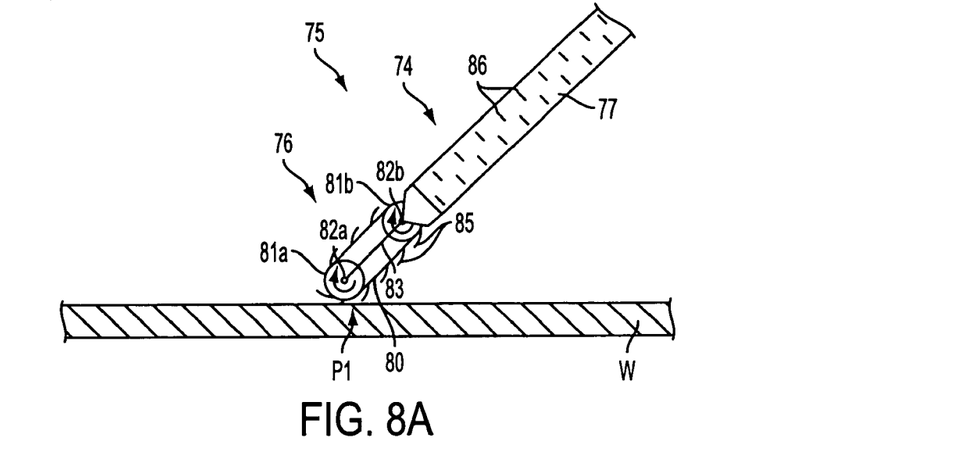
FIGS. 8A-8D are side views of alternative apparatus for forming a gastrointestinal fold.

Referring now to FIG. 8A, an alternative embodiment of apparatus for forming a tissue fold, constructed in accordance with the principles of the present invention, is described. Apparatus 75 comprises treadmill assembly 76 disposed at distal tip 74 of flexible tube 77. Flexible tube 77 is configured to be inserted through a patient's mouth, esophagus and into the stomach. Treadmill assembly 76 comprises conveyor 80 that circles around a pair of hubs 81a and 81b. Hubs 81a and 81b rotate about axles 82a and 82b, respectively, and are interconnected by bracket 83. A plurality of barbs or needles 85 are disposed at substantially regular intervals around the circumference of conveyor 80.

Flexible tube 77 preferably includes a plurality of through-wall slots 86 to enhance flexibility of the tube, yet maintain torqueability. Preferably, flexible tube 77 is made from stainless steel with an etched or laser-cut slot pattern. Preferably, the slot pattern is a sinusoidal repeating pattern of slots perpendicular to the longitudinal axis of the tube.

Figure 8B:
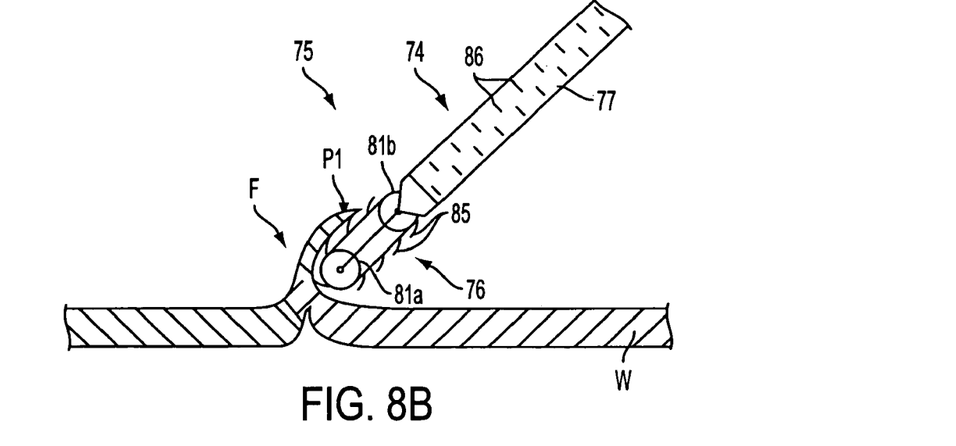
Figure 8C:
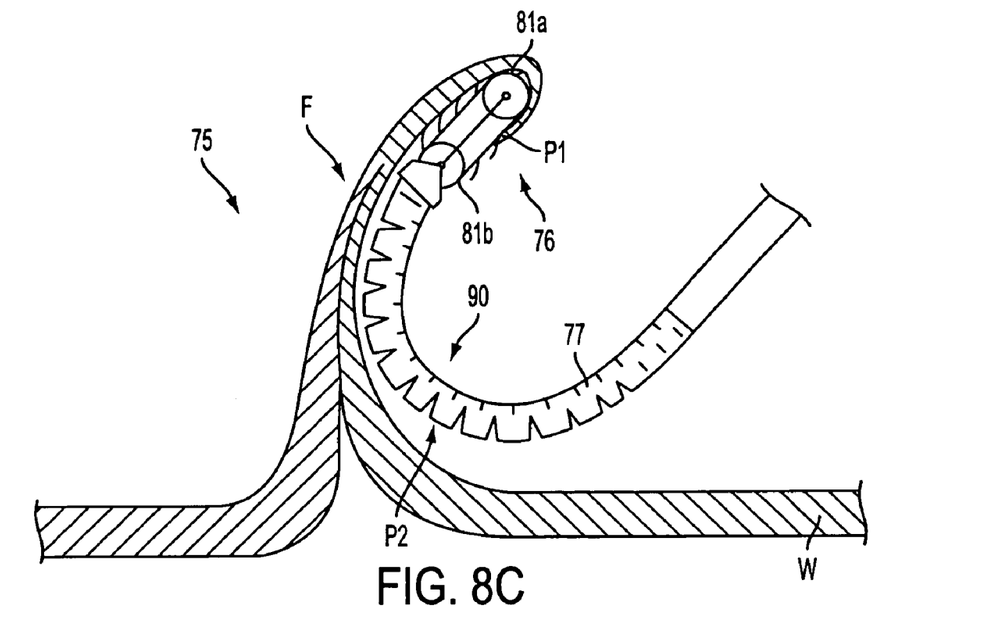
Figure 8D:
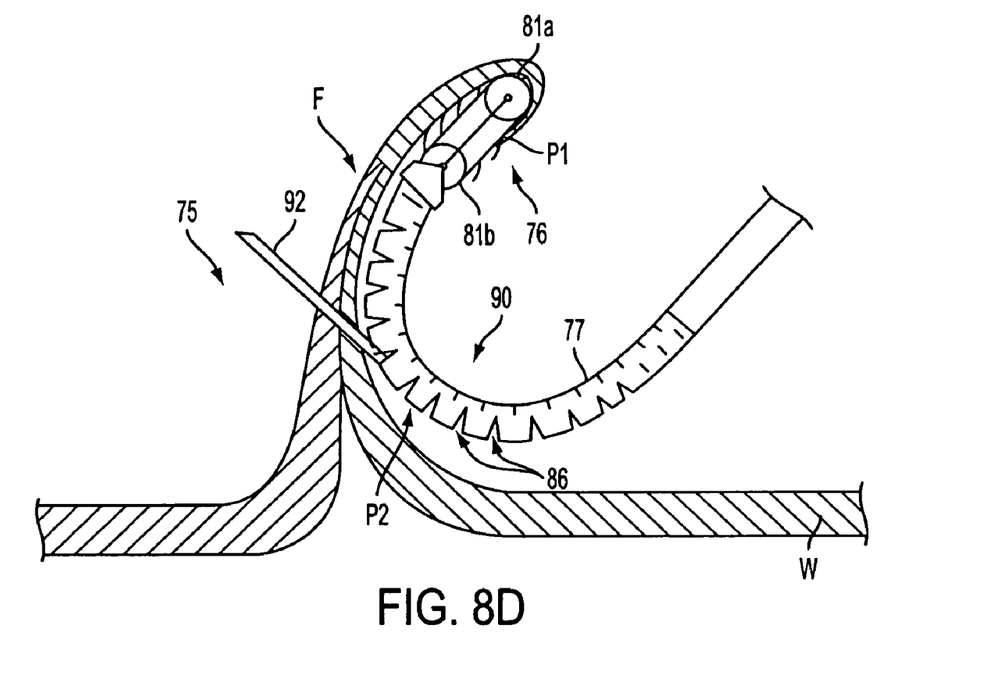
Figure 9:
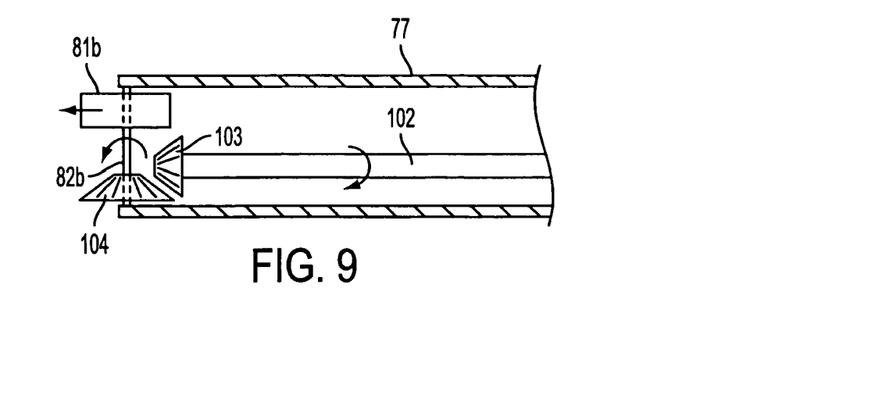
FIG. 9 is a cross-sectional view of the apparatus of FIGS. 8A-8D.

Referring to FIGS. 8 and 9, transmission of motive force to treadmill assembly 76 is described. In particular, drive shaft 102 disposed within flexible tube 77 is coupled to a manual knob or motor located at the proximal end of the catheter. The distal tip of drive shaft 102 is provided with beveled gear 103 that meshes with beveled gear 104 provided on axle 82b. Accordingly, rotation of beveled gear 103 is transmitted to beveled gear 104, thereby causing axle 82b to rotate. Axle 82b in turn rotates hub 81b, actuating conveyor 80. The direction of conveyor 80 may be reversed by reversing the rotation of drive shaft 102.

Referring again to FIGS. 8A-8D, a method of forming a gastrointestinal tissue fold F using apparatus 75 is described. In FIG. 8A, flexible tube 77 is positioned transesophageally so that treadmill assembly 76 contacts tissue wall W. Preferably, contact should be made at an angle relative to the tissue wall W. For example, an angle of approximately 45 degrees is depicted in FIG. 8A, while many other angles may be used without departing from the scope of the present invention.

When treadmill assembly 76 contacts tissue wall W, needle 85 engages the tissue at contact point P1 as the needle moves around distal hub 81a. As depicted in FIG. 8B, as the needle moves away from distal hub 81a, tissue wall W is pulled towards proximal end 81b, thereby forming a small tissue fold F. As the treadmill assembly continues to turn, subsequent needles 85 engage the tissue wall so that it becomes securely engaged to treadmill assembly 76 along the length of conveyor 80.

As depicted in FIG. 8C, once tissue wall W is securely engaged to treadmill assembly 76, distal end 74 of flexible tube 77 may be articulated in bendable section 90, thereby moving treadmill assembly 76 away from tissue wall W. The articulation of flexible tube 77 may be accomplished using a control wire and actuator disposed at the proximal end of the catheter, as described for the embodiment of FIG. 1. By moving the treadmill assembly away from tissue wall W, additional tissue is pulled proximally and tissue fold F becomes elongated.

In FIG. 8D, tissue fold F is stretched across bendable section 90 of flexible tube 77 to create contact point P2. This permits a sharpened needle or obturator to be extended through one of slots 86 of bendable section 90 and across all four layers of the tissue wall W. Advantageously, stretching of tissue fold F across bendable section 90 permits an anchor to be ejected through both the muscularis and serosa layers, thus providing a durable foundation for gastrointestinal tissue approximation. For example, needle 92 may be extended through slot 86 in bendable section 90, and through the base of tissue fold F, and an anchor assembly (such as described with respect to FIGS. 4A-4C) may be ejected from needle 92 to secure the fold. Alternatively, an obturator (such as described with respect to FIGS. 5A and 5B) may be used to pierce the tissue fold at contact point P2 and deliver the anchor assembly. Treadmill assembly 76 may be disengaged from tissue wall W by reversing the rotation of proximal hub 81b.

Referring now to FIG. 1A, a further alternative embodiment of apparatus for forming a tissue fold in accordance with the principles of the present invention is described. Apparatus 100 comprises tissue grabbing assembly 18' coupled to the distal end of a flexible tube 77', such as described with respect to the embodiment of FIG. 8. Flexible tube 77' preferably includes a plurality of through-wall slots 86' to enhance flexibility of the tube, yet maintain torqueability. In addition, flexible tube 77' may be made from stainless steel with an etched or laser-cut slot pattern, such as a sinusoidal repeating pattern of slots perpendicular to the longitudinal axis of the tube.

Tissue grabbing assembly 18' is similar to that described with respect to the embodiment of FIG. 1, and comprises a pair of jaws 28a', 28b' arranged to rotate about pivot point 29' between an open configuration and a closed configuration. Each of jaws 28a', 28b' preferably includes sharpened teeth 33' disposed near its distal end to facilitate grasping tissue wall W.

Figure 10A:
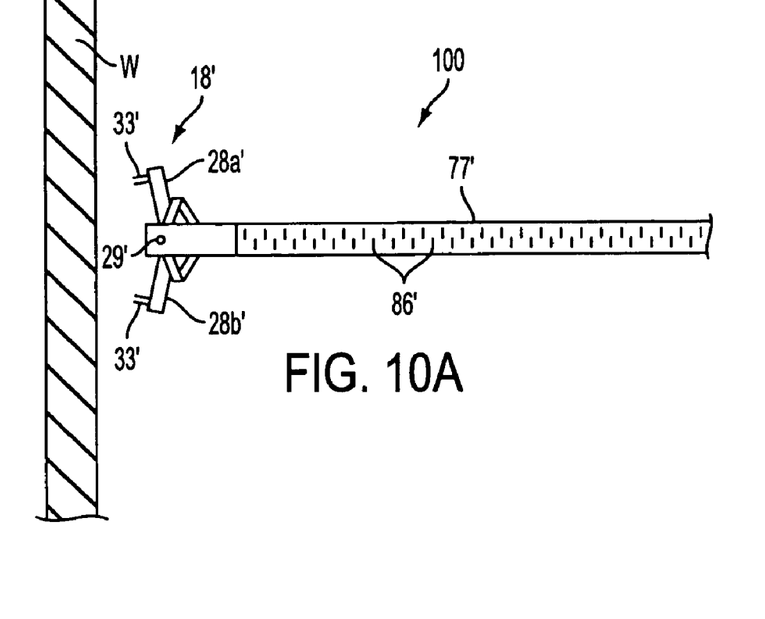
FIGS. 10A-10D are side views of a further alternative apparatus for forming a gastrointestinal tissue fold in accordance with the principles of the present invention.
Figure 10B:
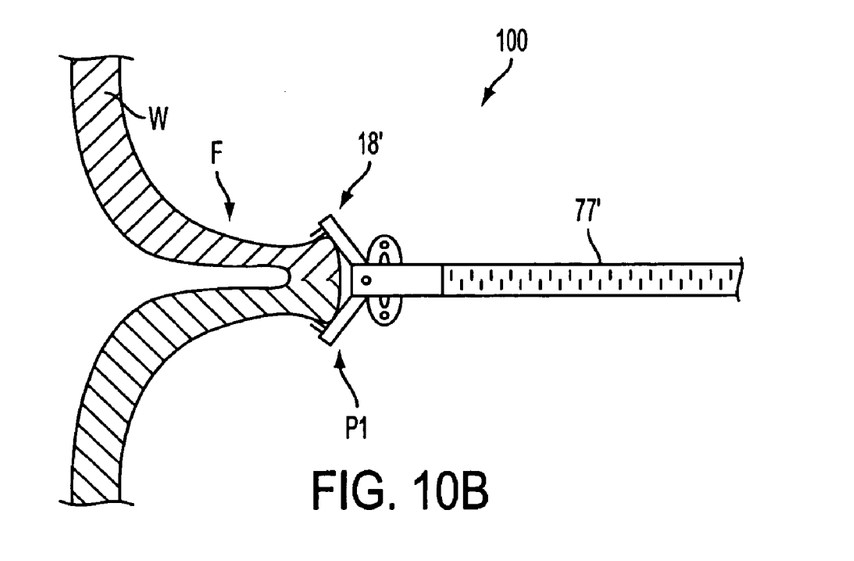

With respect to FIG. 10A, tissue grabbing assembly 18' is positioned transesophageally adjacent to tissue wall W and jaws 28a', 28b' are moved to the open position. Tissue grabbing assembly 18' then is moved into contact with tissue wall W. As depicted in FIG. 10B, tissue grabbing assembly 18' is used to grab the tissue wall at a first contact point P1. After capturing a portion of tissue wall W within jaws 28a', 28b', flexible tube 77' is urged proximally to stretch tissue wall W and create tissue fold F.

Figure 10C:
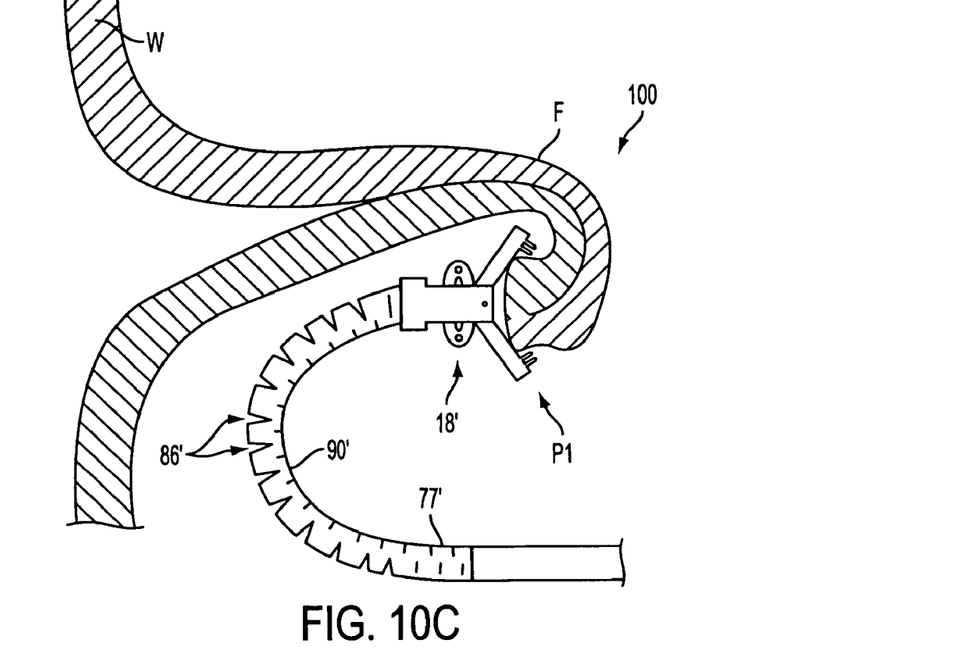

Referring to FIG. 10C, once tissue fold F is formed, the distal end of flexible tube 77' is articulated about bendable section 90' to move tissue grabbing assembly 18' away from tissue wall W. Articulation of flexible tube 77' may be controlled using an actuator disposed at the proximal end of the catheter, thus causing tissue fold F to become elongated.

Figure 10D:
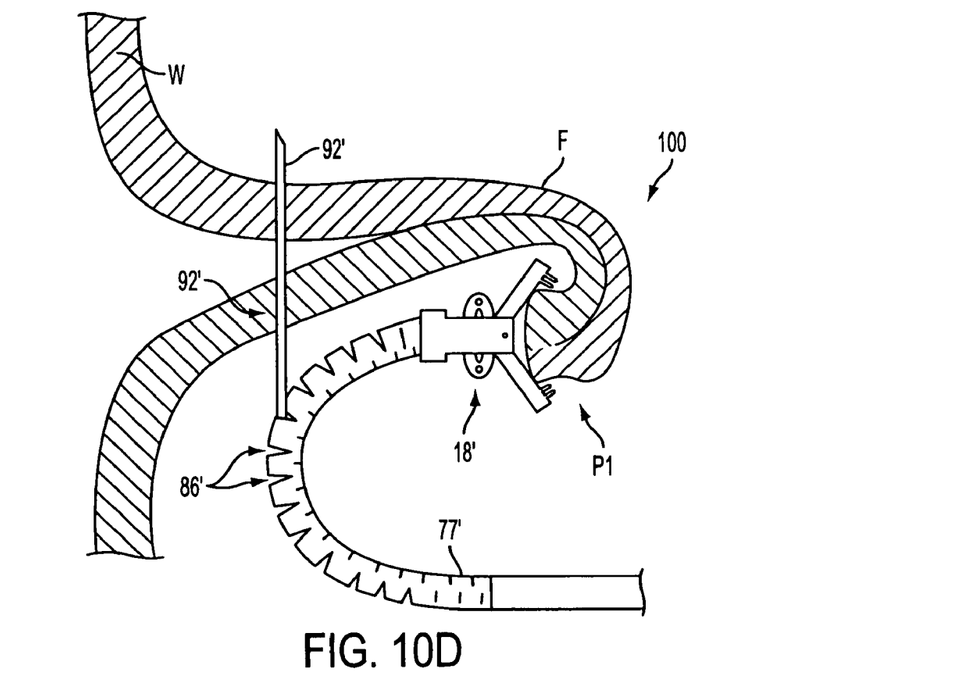

In FIG. 10D, tissue fold F is shown stretched across bendable section 90' so that a sharpened needle or obturator may be extended from one of slots 86' in bendable section 90' and across all four layers of the tissue wall W. Needle 92' then may be extended from slot 86' in bendable section 90' through contact point P2 and tissue fold F. An anchor assembly (e.g., as described with respect to FIGS. 4A-4C) then may be ejected from needle 92' to secure the fold. Alternatively, an obturator (e.g., as described with respect to FIGS. 5A and 5B) may be used to pierce the tissue fold at contact point P2 and deliver the anchor assembly.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus comprising:
    an elongated shaft having a proximal end, a distal end, and a longitudinal axis;
    a first tube having a bendable distal section located at or near the distal end of the elongated shaft, the bendable distal section having a first state generally aligned with or parallel to the longitudinal axis of the elongated shaft, and a second state in which the bendable distal section defines an arcuate shape relative to the longitudinal axis of the elongated shaft;
    a hollow needle having a piercing tip, the piercing tip having a first position located within the first tube and a second position extended from the first tube;
    at least one anchor assembly within the hollow needle;
    a second tube having a tissue grabbing member located at or near the distal end of the elongated shaft; and
    a link having a first end pivotally attached to the first tube at or distal to the bendable distal section, and having a second end pivotally attached to the second tube at or near the tissue grabbing member, with the link limiting movement of the tissue grabbing member relative to the first tube.

2. The apparatus of claim 1, wherein the tissue grabbing member comprises one or more needles or barbs.

3. The apparatus of claim 1, wherein the tissue grabbing member comprises a pair of jaws movable between an open position and a closed position.

4. The apparatus or claim 1, wherein the anchor assembly comprises a pair of anchors coupled by a suture or wire.

5. The apparatus of claim 1, further comprising a push rod within the hollow needle, with the anchor assembly being located between the push rod and the piercing tip of the needle.

* * * * *

UNITED STATES PATENT AND TRADEMARK OFFICE
CERTIFICATE OF CORRECTION

PATENT NO.       : 7,618,426 B2  Page 1 of 1
APPLICATION NO.  : 10/639162
DATED            : November 17, 2009
INVENTOR(S)      : Ewers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1025 days.

Signed and Sealed this

Twenty-sixth Day of October, 2010

David J. Kappos
*Director of the United States Patent and Trademark Office*